(12) United States Patent
Takeda et al.

(10) Patent No.: US 7,824,663 B2
(45) Date of Patent: Nov. 2, 2010

(54) LIP GLOSS COMPOSITION

(75) Inventors: Kyoichi Takeda, Katori-gun (JP); Yuki Kokeguchi, Katori-gun (JP); Mari Yoshida, Katori-gun (JP); Kiyoshi Maeno, Chigasaki (JP)

(73) Assignee: Kokyu Alcohol Kogyo Co., Ltd., Katori-Gun (JP)

( * ) Notice: Subject to any disclaimer, the term of this patent is extended or adjusted under 35 U.S.C. 154(b) by 983 days.

(21) Appl. No.: 11/371,290

(22) Filed: Mar. 9, 2006

(65) Prior Publication Data

US 2006/0204460 A1 Sep. 14, 2006

Related U.S. Application Data

(60) Provisional application No. 60/719,215, filed on Sep. 22, 2005.

(30) Foreign Application Priority Data

Mar. 10, 2005 (JP) .............................. 2005-110296

(51) Int. Cl.
*A61K 8/37* (2006.01)
(52) U.S. Cl. ...................................... 424/64; 424/401
(58) Field of Classification Search ............. 424/401, 424/64
See application file for complete search history.

(56) References Cited

U.S. PATENT DOCUMENTS 4,780,145 A * 10/1988 Mori et al. ............... 106/162.1
6,042,842 A * 3/2000 Lemann et al. ............ 424/401
6,592,857 B2 * 7/2003 Lawson et al. ......... 424/70.122
2005/0191327 A1 * 9/2005 Yu et al. .................... 424/401

FOREIGN PATENT DOCUMENTS

| JP | A 2002-275020 | 9/2002 |
| JP | A 2002-338425 | 11/2002 |
| JP | A 2003-226609 | 8/2003 |
| JP | A 2004-256515 | 9/2004 |
| JP | A 2005-179377 | 7/2005 |

OTHER PUBLICATIONS

Takeda, K. et al., "Cosmetic", Jul. 7, 2005, JP 2005-179377, machine translation.*

* cited by examiner

*Primary Examiner*—Gina C Yu
(74) *Attorney, Agent, or Firm*—Oliff & Berridge, PLC

(57) ABSTRACT

The present invention provides a lip gloss composition having appropriate adhesion, spreadability, durability, practical properties such as gloss on the applied surface, storage stability, and safety to skin.

A lip gloss composition, comprising (A) 20 to 60 parts by mass of polyglyceryl-2 dimer dilinoleate isostearate and/or hydrogenated polyisobutene; (B) 0.5 to 1.0 part by mass of a polamide resin with an amide terminal group and/or a polyamide resin with an ester terminal group; (C) 1.75 to 7.0 parts by mass of a dextrin ester of an aliphatic: (D) 20 to 55 parts by mass of at least one hydroxy compound selected from the group consisting of diisostearyl malate, polyglyceryl-2 diisostearate polyglyceryl-2 triisostearate, dipentaerythrityl diisostearate and dipentaerylthrityl trisostearate; and (E) 15 to 40 parts by mass of a liquid oil having a viscosity of 5 to 400 mPa·s at 25 degrees C., wherein a total amount of (A) to (E) is 100 parts by mass and the ratio by mass (C)/(B) is 3.5 to 7.0.

8 Claims, No Drawings

LIP GLOSS COMPOSITION

CROSS REFERENCES

This application claims the benefits of U.S. Provisional Patent Application No. 60/719,215 filed on Sep. 22, 2005 and Japanese Patent Application No. 2005-110296 filed on Mar. 10, 2005, the contents of which are herein incorporated by references.

FIELD OF THE INVENTION

This invention relates to a lip gloss composition, more specifically, a lip gloss composition having practical properties such as appropriate adhesion, spreadability, durability, and gloss on surface with an applied lip gloss composition, storage stability, and safety to skin.

PRIOR ART

Lip glosses are known cosmetics that comprise a liquid oil with high viscosity and adhesion, a thickening agent, and also various kinds of pigments and used to provide lips with gloss and color. They are known from Japanese Patent Application Laid-Open Nos. 2002-275020, 2003-226609, and 2004-256515.

The applicant of the present invention has developed a hydroxyl compound having high viscosity and high adhesion that is derived from digylcerin, isostearic acid, and dimer acid, and proposed lip glosses that comprise this hydroxyl compound and are smoothly applied and good in gloss and adhesion (see Japanese Patent Application Laid-Open 2005-179377).

SUMMARY OF THE INVENTION

The object of the present invention is to provide a lip gloss composition having practical properties such as appropriate adhesion, spreadability, durability, and gloss on surface with an applied lip gloss composition, storage stability, and safety to skin.

The inventors have found that a lip gloss composition comprising the following ingredients has the above-described properties and completed the present invention.

The present invention is a lip gloss composition comprising (A) 20 to 60 parts by mass of polyglyceryl-2 dimer dilinoleate isostearate and/or hydrogenated polyisobutene;

(B) 0.5 to 1.0 part by mass of a polyamide resin with an amide terminal group and/or a polyamide resin with an ester terminal group;

(C) 1.75 to 7.0 parts by mass of a dextrin ester of an aliphatic acid;

(D) 20 to 55 parts by mass of at least one hydroxy compound selected from the group consisting of diisostearyl malate, polyglyceryl-2 diisostearate, polyglyceryl-2 triisostearate, dipentaerythrityl diisostearate and dipentaerylthrityl trisostearate; and (E) 15 to 40 parts by mass of a liquid oil having a viscosity of 5 to 400 mPa·s at 25 degrees C., wherein a total amount of (A) to (E) is 100 parts by mass and a ratio by mass, (C)/(B), is 3.5 to 7.0.

DESCRIPTION OF THE PREFERRED EMBODIMENTS

In the present lip gloss composition, the upper limit of the amount of (A) is 60 parts by mass, preferably 50 parts by mass, and more preferably 45 parts by mass, whereas the lower limit is 20 parts by mass, preferably 25 parts by mass, and more preferably 30 parts by mass. If the amount of (A) exceeds the aforementioned upper limit, the adhesion is too strong and the spreadability is poor, which results in sticky feeling. If the amount is lower than the aforementioned lower limit, the gloss on the surface with an applied lip gloss composition and the adhesion are poor.

The upper limit of the amount of (B) is 1.0 part by mass, preferably 0.9 part by mass, and more preferably 0.8 part by mass, whereas the lower limit is 0.5 part by mass, preferably 0.6 part by mass, and more preferably 0.7 part by mass. If the amount of (B) exceeds the aforementioned upper limit, the storage stability is poor. If the amount is lower than the aforementioned lower limit, the spreadability of the composition is poor.

The upper limit of the amount of (C) is 7.0 parts by mass, preferably 5.0 parts by mass, and more preferably 4.0 parts by mass, whereas the lower limit is 1.75 parts by mass, preferably 2.0 parts by mass, and more preferably 3.0 parts by mass. If the amount of (C) exceeds the aforementioned upper limit, the spreadability is poor, which results in sticky feeling. If the amount is lower than the aforementioned lower limit, the adhesion is poor. The amount of (C) is such that the ratio, (C)/(B), is 3.5 to 7.0, preferably 4.0 to 6.5, and more preferably 4.5 to 6.0. If the ratio exceeds the aforementioned upper limit, the spreadability is poor. If the amount is lower than the aforementioned lower limit, the viscosity, the adhesion, and the storage stability are poor.

The upper limit of the amount of (D) is 55 parts by mass, preferably 50 parts by mass, and more preferably 40 parts by mass, whereas the lower limit is 20 parts by mass, preferably 30 parts by mass, and more preferably 35 parts by mass. If the amount exceeds the aforementioned upper limit, the adhesion is too strong and the spreadability is poor, which results in stick feeling. If the amount is lower than the aforementioned lower limit, the storage stability is poor.

The upper limit of the amount of (E) is 40 parts by mass, preferably 35 parts by mass, and more preferably 30 parts by mass, whereas the lower limit is 15 parts by mass, preferably 20 parts by mass, and more preferably 25 parts by mass. If the amount exceeds the aforementioned upper limit, the viscosity of the composition is poor. If the amount is lower than the aforementioned lower limit, the spreadability is poor, which results in sticky feeling.

The present lip gloss composition comprises (A), (B), (C), (D), and (E) in the above-described amounts so that the total amount of (A) to (E) is 100 parts by mass.

Polyglyceryl-2 dimer dilinolate isostearate, (A), is known also as a (polyglyceryl-2 isostearate/dimer dilinolate) copolymer and disclosed in Japanese Patent Application Laid-Open 2005-179377. The compound is obtained by condensation of diglycerin, isostearic acid, and dimer dilinoleic acid. The hydrogenated polyisobutene is a known material and commonly used as an ingredient in cosmetics.

The polyamide resin with an amide terminal group and/or the polyamide resin with an ester terminal group, (B), are disclosed in Japanese Patent Application Laid-Open 2005-179377. As examples of the polyamide resin with an amide terminal group, mention may be made of ethylenediamine/hydrogenated dimer dilinoleate copolymer bis-di-$C_{14}$-$C_{18}$ alkyl amine, INCI name. As examples of the polyamide resin with an ester terminal group, mention may be made of ethylenediamine/stearyl dimer tallate copolymer, INCI name. Commercial products of the former include Silver Clear A200V and Silver Clear A2614V, trademarks of Arizona Chemical Co. Ltd. Commercial products of the latter include Uniclear, trademark of Arizona Chemical Co. Ltd.

The dextrin ester of an aliphatic acid, (C), is known and commonly used as an ingredient in cosmetics. For example, mention may be made of dextrin palmitate, dextrin palmitate/octanoate. As examples of commercial products, mention may be made of Rheopearl KL and Rheopearl TT (trademarks of Chiba Seifun).

(D) is at least one hydroxy compound selected from the group consisting of diisostearyl malate, polyglyceryl-2 diisostearate, polyglyceryl-2 triisostearate, dipentaerythrityl diisostearate, and dipentaerythrityl trisostearate. These materials are commonly used in cosmetics.

The liquid oil having a viscosity of from 5 to 400 mPa·s at 25 degrees C., (E), is known and commonly used in cosmetics. The viscosity of the liquid oil at 25 degrees C. is preferably 8 to 350 mPa·s, and more preferably 12 to 300 mPa·s. If the viscosity exceeds the aforementioned upper limit, the spreadability is poor, which results in sticky feeling. If the viscosity is lower than the aforementioned lower limit, the viscosity of the composition is poor. The viscosity is measured on a Brookfield viscometer using No. 2 spindle at 12 rpm. Examples of (E) include isononyl ethylhexanoate (5 mPa·s), isononyl isononanoate (6 mPa·s), isopropyl palmitate (7 mPa·s), isopropyl isostearate (10 mPa·s), hexyldecyl ethylhexanoate (11 mPa·s), isotridecyl isononanoate (12 mPa·s), neopentylglycol diethylhexanoate (13 mPa·s), cetyl ethylhexanoate (13 mPa·s), isostearyl neopentanoate (15 mPa·s), octyldodecyl neopentanoate (15 mPa·s), neopentylglycol dicaprate (19 mPa·s), glycerol tri(caprylate/caprate) (25 mPa·s), octyldodecyl neodecanoate (25 mPa·s), octyldodecyl myristate, squalane (32 mPa·s), hexyldecyl isostearate (34 mPa·s), triethyl hexanoin (35 mPa·s), isostearyl isostearate (40 mPa·s), trimethylolpropane triethylhexanoate (52 mPa·s), ethylhexyl hydroxystearate (64 mPa·s), octyldodecyl stearoyloxystearate (90 mPa·s), pentaerythrityl tetraethylhexanoate (110 mPa·s), trimethylolpropane triisostearate (180 mPa·s), triisostearine (185 mPa·s), pentaerythrityl tetraisostearate (290 mPa·s), and diisopropyl dilinoleate (310 mPa·s). The values in parentheses are viscosities at 25 degrees C.

In addition to the aforementioned (A) to (E), the present lip gloss composition may comprise conventional additives that are commonly used in lip glosses in such a range of amount that the effects of the present invention are not impaired. Examples of the additives include pigments such as, for instance, coloring pigments such as Red No. 201 and Red No. 202, white pigments such as titanium oxide, and extender pigments such as silica; dyestuffs such as Blue No. 1, Red No. 218, and Red No. 225; lame agents; pearlescent agents; antioxidant agents; anti-septic agents; ultraviolet rays absorbers; perfumes; cooling agents; anti-inflammatory agents; purified water; plant oils; mineral oils; solid waxes; and silicone oils.

The present lip gloss composition may be prepared according to known methods. For instance, (A) to (E) are mixed together and dissolved under stirring, preferably, at a temperature of from 90 to 100 degrees C. to obtain a homogenous mixture, which is then subjected to defoaming. The lip gloss composition is prepared by cooling the mixture to ambient temperature. When a colored lip gloss composition is desired, a pigment is kneaded with an oil separately and added to the aforementioned homogeneously dissolved mixture, preferably, at a temperature of from 90 degrees C. to 100 degrees C. Then the mixture is dissolved under stirring at the same temperature to obtain a homogeneous mixture, which is then subjected to defoaming. The lip gloss composition is prepared by cooling the mixture to ambient temperature.

In the following Examples, the present invention will be elucidated further in detail without being limited thereto.

EXAMPLES

In the Examples and the Comparative Examples, the practical properties, storage stability and safety to skin were evaluated according to the following evaluation methods.

Evaluation Methods

1. Practical Properties

Subjects were 20 people, i.e. 10 males and 10 females. Each subject used the lip gloss compositions obtained in the Examples and the Comparative Examples 5 times in 10 days, and evaluated their adhesion, spreadability, durability (non-transferring property), and gloss on the surface with an applied lip gloss composition. Each evaluation item was given a score of from 5 to 0 in six steps in descending order of each desired property. The score was averaged among all of the subjects. The evaluation "G" was assigned for an average score of 3.5 to 5.0; "M" for an average score of 2.5 to 3.4; and "B" for an average score of 0 to 2.4.

2. Storage Stability

The lip gloss compositions obtained in the Examples and the Comparative Examples were stored at 45 degrees C. in a temperature-controlled room for three months. Subsequently, the compositions were stored at −5 degrees C. for one day, and then at 45 degrees C. for two days in the temperature controlled room. This operation was repeated 5 times and then the compositions were evaluated for occurrence of separation, discoloration, and smelling. When no abnormality was observed, the composition was evaluated as good and given the rate "G". When minor abnormality was observed but it was thought that the composition had practically no problems, the composition was evaluated as "M". When abnormality was observed, the composition was evaluated as bad, and given "B".

3. Safety to Skin

Subjects were twenty people, i.e. ten males and ten females. 0.05 g of the lip gloss composition obtained in the Example or the Comparative Example was applied to a circular patch with cotton lint of 1.0 cm diameter, and then the patch was applied to the forearm flexor of each subject and left for 24 hours. The patch was removed and the skin was examined 1 hour later and 24 hours later to rate the skin conditions of each subject according to the following standards. When the results were different between 1 hour later and 24 hours later, the stronger response was used for rating. When the 20 subjects exhibited (−), the evaluation was "G"; when 1 to 2 subjects exhibited (±) and the other subjects exhibited (−), the evaluation was "M"; and when more than three subjects exhibited (±) and the other subjects exhibited (−) or when one or more subjects exhibited (+) to (+++), the evaluation was "B".

Rating Standards

| Skin Conditions | Rating |
| --- | --- |
| Erythema, edema, and blister: | (+++) |
| Erythema, and edema: | (++) |
| Erythema: | (+) |
| Mild erythema: | (±) |
| No erythema, and no edema: | (−) |

Examples 1-5

The ingredients were mixed in the amounts described in Table 1 and dissolved under stirring at about 100 degrees C. to obtain a homogeneous mixture. The mixture was cooled to about 30 degrees C. to obtain a lip gloss composition. The evaluation tests were performed on the lip gloss compositions. The results are as shown in Table 1.

TABLE 1

|   |   | Example 1 | Example 2 | Example 3 | Example 4 | Example 5 |
|---|---|---|---|---|---|---|
| A | Polyglyceryl-2 dimer dilinoleate isostearate | 40.0 | 30.0 | 20.0 | 35.0 |  |
|   | Hydrogenated polyisobutene |  | 20.0 |  |  | 45.0 |
| B | Polyamide with an amide terminal group | 0.8 | 0.5 | 1.0 |  | 0.35 |
|   | Polyamide with an ester terminal group |  |  |  | 0.6 | 0.35 |
| C | Dextrin palmitate |  | 2.5 |  |  | 3.15 |
|   | Dextrin palmitate/octanoate | 5.0 |  | 3.5 | 3.6 |  |
| D | Diisostearyl malate | 5.0 |  | 10.0 |  | 15.0 |
|   | Polyglyceryl-2 diisostearate | 25.0 |  | 20.0 | 19.7 |  |
|   | Polyglyceryl-2 triisostearate |  | 25.0 | 20.0 | 6.0 | 12.05 |
| E | Isononyl isononanoate |  |  |  |  | 10.0 |
|   | Ethylhexyl hydroxystearate |  |  |  | 20.0 |  |
|   | Octyldodecyl stearoyloxystearate | 12.2 |  |  |  |  |
|   | Diisopropyl dilinoleate |  |  |  | 10.0 |  |
|   | Neopentyl glycol diethylhexanoate |  |  | 12.9 |  |  |
|   | Glycerol tri(caprylate/caprate) |  |  | 12.6 |  |  |
|   | Trimethylolpropane triisostearate |  |  |  | 5.1 |  |
|   | Triethyl hexanoin |  | 22.0 |  |  |  |
|   | Pentaerythrityl tetraisostearate | 12.0 |  |  |  |  |
|   | Pentaerythrityl tetraethylhexanoate |  |  |  |  | 14.1 |
| Other ingredients | Silica dimethyl silylate | 1.0 | 0.7 | 0.5 |  | 0.8 |
|   | Octyl methoxycinnamate |  | 0.5 | 0.5 |  |  |
|   | d-δ-Tocopherol | 0.1 | 0.1 | 0.1 | 0.1 | 0.1 |
|   | (B)/(C) | 1/6.3 | 1/5.0 | 1/3.5 | 1/6.0 | 1/4.5 |
| Practical properties | Adhesion | G | G | G | G | G |
|   | Spreadability | G | G | G | G | G |
|   | Durability | G | G | G | G | G |
|   | Gloss of the surface | G | G | G | G | G |
|   | Storage stability | G | G | G | G | G |
|   | Safety to skin | G | G | G | G | G |

The amounts of the ingredients in Table 1 are indicated in part by mass. The ratio, (B)/(C), is given by mass.

Examples 6-10

The pigments, i.e. titanium oxide, Red No. 201, Red No. 202, Red No. 1, Blue No. 1, and Red No. 225, were kneaded in the amounts in Table 2 at 50 degrees C. with a three-roll kneader. Separately, the other ingredients in Table 2 were mixed in the amounts described and dissolved at about 100 degrees C. under stirring to obtain a homogeneous mixture. To the mixture, the pigments kneaded beforehand as described above were added and mixed further at the same temperature. The mixture thus obtained was cooled to about 30 degrees C. to obtain a lip gloss composition. The evaluation tests were performed on the lip gloss compositions. The results are as shown in Table 2.

TABLE 2

|   |   | Example 6 | Example 7 | Example 8 | Example 9 | Example 10 |
|---|---|---|---|---|---|---|
| A | Polyglyceryl-2 dimer dilinoleate isostearate | 40.0 | 30.0 | 25.0 | 46.0 | 15.0 |
|   | Hydrogenated polyisobutene |  | 15.0 |  |  | 40.0 |
| B | Polyamide with an amide terminal group | 1.0 | 1.0 | 0.6 |  | 0.4 |
|   | Polyamide with an ester terminal group |  |  |  | 0.6 | 0.3 |
| C | Dextrin palmitate |  |  | 5.5 |  | 3.15 |
|   | Dextrin palmitate/octanoate | 7.0 |  | 3.9 | 3.6 |  |
| D | Diisostearyl malate | 5.0 |  | 10.0 |  | 10.0 |
|   | Polyglyceryl-2 diisostearate | 25.0 |  | 15.0 | 15.0 |  |
|   | Polyglyceryl-2 triisostearate |  | 25.0 | 20.0 | 5.0 | 10.0 |
| E | Isotridecyl isononanoate |  |  |  |  | 3.0 |
|   | Ethylhexyl hydroxystearate |  |  |  | 10.80 |  |
|   | Octyldodecyl stearoyloxystearate | 11.1 |  |  |  |  |
|   | Diisopropyl dilinoleate |  |  |  | 10.0 |  |
|   | Neopentylglycol diethylhexanoate |  |  | 7.7 |  |  |
|   | Glycerol tri(caprylate/caprate) |  |  | 12.80 |  |  |
|   | Trimethylolpropane triisostearate |  | 11.50 |  | 5.0 |  |
|   | Triethyl hexanoin |  |  |  |  | 8.2 |

TABLE 2-continued

|  |  | Example 6 | Example 7 | Example 8 | Example 9 | Example 10 |
|---|---|---|---|---|---|---|
| Other ingredients | Pentaerythrityl tetraisostearate | 10.90 |  | 5.0 | 5.0 |  |
|  | Pentaerythrityl tetraethylhexanoate |  | 12.0 |  |  | 5.0 |
|  | Silica dimethyl silylate | 1.0 | 0.7 | 0.5 |  | 0.8 |
|  | Octyl methoxycinnamate |  |  | 0.5 | 0.5 |  |
|  | d-δ-Tocopherol | 0.1 | 0.1 | 0.1 | 0.1 | 0.1 |
|  | Titanium oxide | 0.12 | 0.01 | 0.01 |  |  |
|  | Red No. 201 | 0.01 |  | 0.14 |  |  |
|  | Red No. 202 | 0.02 | 0.13 | 0.002 |  |  |
|  | Blue No. 1 |  | 0.01 |  |  |  |
|  | Red No. 225 |  |  |  | 0.01 | 0.05 |
|  | (B)/(C) | 1/7.0 | 1/5.5 | 1/6.5 | 1/6.0 | 1/4.5 |
| Practical properties | Adhesion | G | G | G | G | G |
|  | Spreadability | G | G | G | G | G |
|  | Durability | G | G | G | G | G |
|  | Gloss of the surface | G | G | G | G | G |
|  | Storage stability | G | G | G | G | G |
|  | Safety to skin | G | G | G | G | G |

The amounts of the ingredients in Table 2 are indicated in part by mass. The ratio, (B)/(C), is given by mass.

Examples 11 to 13

The pigments, i.e. titanium oxide, Red No. 201, Red No. 202, and Blue No. 1, were kneaded in the amounts in Table 3 at about 50 degrees C. with a three-roll kneader. Separately, the other ingredients than the aforementioned pigments in Table 3, than the lame agents I and II, and than the pearlescent agent were mixed in the described amounts and, then, dissolved at about 100 degrees C. under stirring to obtain a homogeneous mixture. To the mixture, the pigments kneaded beforehand as described above, the lame agents I and II, and the pearlescent agent were added and mixed further at the same temperature to obtain a homogeneous mixture. The resulting mixture was cooled to about 30 degrees C. to obtain a lip gloss composition. The Evaluation tests were performed on the lip gloss composition. The results are as shown in Table 3. The lame agent I was Iridescent Glitter IF 8101, trademark of Dia Chemco Co. Ltd., containing laminate of PET/methyl polymethacrylate as a major component. The lame agent II was Prominence RYH, trademark of TOPY Industries Ltd., containing synthetic mica, titanium oxide, and iron oxide as major components. The pearlescent agent was Timiron Star Luster MP-115, trademark of Merck Co. Ltd., containing titanium oxide and mica as major components.

TABLE 3

|  |  | Example11 | Example12 | Example13 |
|---|---|---|---|---|
| A | Polyglyceryl-2 dimer dilinoleate isostearate | 40.00 | 30.00 | 25.00 |
|  | Hydrogenated polyisobutene |  | 15.00 |  |
| B | Polyamide with an amide terminal group | 0.50 | 0.70 |  |
|  | Polyamide with an ester terminal group |  |  | 0.60 |
| C | Dextrin palmitate |  | 3.00 |  |
|  | Dextrin palmitate/octanoate | 1.80 |  | 3.00 |
| D | Diisostearyl malate | 10.00 | 5.05 | 7.00 |
|  | Polyglyceryl-2 diisostearate | 20.00 |  | 15.00 |
|  | Polyglyceryl-2 triisostearate |  | 20.00 | 18.00 |
| E | Octyldodecyl stearoyloxystearate | 10.95 |  |  |
|  | Neopentylglycol diethylhexanoate |  |  | 6.80 |
|  | Glycerol tri(caprylate/caprate) |  |  | 12.30 |
|  | Trimethylolpropane triisostearate |  | 11.00 |  |
|  | Pentaerythrityl tetraisostearate | 14.00 |  | 6.548 |
|  | Pentaerythrityl tetraethylhexanoate |  | 12.00 |  |
| Other ingredients | Silica dimethyl silylate |  |  | 0.50 |
|  | Microcrystalline wax | 2.00 |  | 3.00 |
|  | Beeswax |  | 2.00 |  |
|  | Vaseline |  |  | 1.00 |
|  | Octyl methoxycinnamate |  | 0.50 | 0.50 |
|  | d-δ-Tocopherol | 0.10 | 0.10 | 0.10 |
|  | Titanium oxide | 0.12 | 0.01 | 0.01 |
|  | Red No. 201 | 0.01 |  | 0.14 |
|  | Red No. 202 | 0.02 | 0.13 | 0.002 |
|  | Blue No. 1 |  | 0.01 |  |
|  | Lame agent I | 0.50 |  |  |
|  | Lame agent II |  | 0.50 |  |
|  | Pearlescent agent |  |  | 0.50 |
|  | (B)/(C) | 1/3.5 | 1/4.3 | 1/5.0 |
| Practical properties | Adhesion | G | G | G |
|  | Spreadability | G | G | G |

TABLE 3-continued

|  | Example11 | Example12 | Example13 |
|---|---|---|---|
| Durability | G | G | G |
| Gloss of the surface | G | G | G |
| Storage stability | G | G | G |
| Safety to skin | G | G | G |

The amounts of the ingredients in Table 3 are indicated in part by mass. The ratio, (B)/(C), is given by mass.

Comparative Examples 1-3

The procedures of Example 10 were repeated to obtain the lip gloss composition except that the amounts of (B) and (C) were changed. The evaluation tests were performed on the lip gloss compositions. The results are presented in Table 4.

TABLE 4

|  |  | Comparative Example 1 | Comparative Example 2 | Comparative Example 3 |
|---|---|---|---|---|
| A | Polyglyceryl-2 dimer dilinoleate isostearate | 15.0 | 15.0 | 15.0 |
|  | Hydrogenated polyisobutene | 40.0 | 40.0 | 40.0 |
| B | Polyamide with an amide terminal group | 3.85 | 1.1 | 0.23 |
|  | Polyamide with an ester terminal group |  |  | 0.20 |
| C | Dextrin palmitate |  | 2.75 | 3.42 |
| D | Diisostearyl malate | 10.0 | 10.0 | 10.0 |
|  | Polyglyceryl-2 diisostearate |  |  |  |
|  | Polyglyceryl-2 triisostearate | 10.0 | 10.0 | 10.0 |
| E | Isotridecyl isononanoate | 8.0 | 8.0 | 8.0 |
|  | Ethylhexyl hydroxystearate |  |  |  |
|  | Diisopropyl dilinoleate |  |  |  |
|  | Trimethylolpropane triisostearate |  |  |  |
|  | Triethyl hexanoin | 8.2 | 8.2 | 8.2 |
|  | Pentaerythrityl tetraisostearate |  |  |  |
|  | Pentaerythrityl tetraethylhexanoate | 5.0 | 5.0 | 5.0 |
| Other ingredients | Silica dimethyl silylate | 0.8 | 0.8 | 0.8 |
|  | Octyl methoxycinnamate |  |  |  |
|  | d-δ-Tocopherol | 0.1 | 0.1 | 0.1 |
|  | Red No. 225 | 0.05 | 0.05 | 0.05 |
|  | (B)/(C) | 1/0 | 1/2.5 | 1/8.0 |
| Practical properties | Adhesion | M | B | M |
|  | Spreadability | G | M | B |
|  | Durability | M | G | G |
|  | Gloss of the surface | G | G | G |
|  | Storage stability | B | M | M |
|  | Safety to skin | G | G | G |

The amounts of the ingredients in Table 4 are indicated in part by mass. The ratio, (B)/(C), is given by mass.

It is seen from Tables 1-4 that the lip gloss compositions of Examples 1 to 5, 6 to 10, and 11 to 13 have the good practical properties, storage stability, and safety to skin. The composition of Comparative Example 1 had the same formulation as that of Example 10, except that (C) was not formulated and the amount of (B) was increased from 0.7 part by mass to 3.85 parts by mass. The composition of Comparative Example 1 containing no (C) was notably less stable in storage than that of Example 10 and worse in adhesion and durability. The compositions of Comparative Examples 2 and 3 were the same as that of Example 10, except that ratio, (B)/(C), was 1/2.5 and 1/8.0, respectively. The composition of Comparative Example 2, which had a larger (B)/(C) ratio, was notably worse in adhesion and poorer in spreadability and storage stability, compared to that of Example 10. The composition of Comparative Example 3, which had a smaller (B)/(C) ratio, was notably worse in spreadability and poorer in adhesion and storage stability, compared to that of Example 10.

What we claim is:

1. A lip gloss composition, comprising:
   (A) 20 to 60 parts by mass of polyglyceryl-2 dimer dilinoleate isostearate;
   (B) 0.5 to 1.0 part by mass of at least one selected from the group consisting of a polyamide resin with an amide terminal group and a polyamide resin with an ester terminal group;
   (C) 1.75 to 7.0 parts by mass of a dextrin ester of an aliphatic acid;
   (D) 20 to 55 parts by mass of at least one hydroxy compound selected from the group consisting of diisostearyl malate, polyglyceryl-2 diisostearate, polyglyceryl-2 triisostearate, dipentaerythrityl diisostearate, and dipentaerythrityl triisostearate; and
   (E) 15 to 40 parts by mass of a liquid oil having a viscosity of 5 to 400 mPa·s at 25 degrees C.,
   wherein a total amount of (A) to (E) is 100 parts by mass, and a ratio by mass, (C)/(B), is 3.5 to 7.0.

2. The lip gloss composition according to claim 1, comprising 25 to 50 parts by mass of (A), 0.6 to 0.9 part by mass of (B), 2.0 to 5.0 parts by mass of (C), 30 to 50 parts by mass of (D), and 20 to 35 parts by mass of (E).

3. The lip gloss composition according to claim 1, comprising 30 to 45 parts by mass of (A), 0.7 to 0.8 part by mass of (B), 3.0 to 4.0 parts by mass of (C), 35 to 40 parts by mass of (D), and 25 to 30 parts by mass of (E).

4. The lip gloss composition according to claim 1, wherein the ratio by mass, (C)/(B), is 4.0 to 6.5.

5. The lip gloss composition according to claim 1, wherein the ratio by mass, (C)/(B) is 4.5 to 6.0.

6. The lip gloss composition according to claim 1, wherein the viscosity of (E) is 8 to 350 mPa·s at 25 degrees C.

7. The lip gloss composition according to claim 1, wherein the viscosity of (E) is 12 to 300 mPa·s at 25 degrees C.

8. The lip gloss composition according to claim 1, wherein (E) is selected from the group consisting of isononyl ethylhexanoate, isononyl isononanoate, isopropyl palmitate, isopropyl isostearate, hexyldecyl ethylhexanoate, isotridecyl isononanoate, neopentyl glycol diethylhexanoate, cetyl ethylhexanoate, isostearyl neopentanoate, octyldodecyl neopentanoate, neopentyl glycol dicaprate, glycerol tri(caprylate/caprate), octyldodecyl neodecanoate, octyldodecyl myristate, squalane, hexyldecyl isostearate, triethyl hexanoin, isostearyl isostearate, trimethylolpropane triethylhexanoate, ethylhexyl hydroxystearate, octyldodecyl stearoyloxystearate, pentaerythrityl tetraethylhexanoate, trimethylolpropane triisostearate, triisostearine, pentaerythrityl tetraisostearate, and diisopropyl dilinoleate.

* * * * *